US012667264B2

(12) United States Patent

Nitzan

(10) Patent No.: US 12,667,264 B2
(45) Date of Patent: Jun. 30, 2026

(54) METHOD AND APPARATUS FOR EARLY DETECTION OF WORSENING HEART FAILURE

(71) Applicant: AQUAPASS LTD, Or-Akiva (IL)

(72) Inventor: Yaacov Nitzan, Hertzelia (IL)

(73) Assignee: AQUAPASS LTD, Or-Akiva (IL)

( * ) Notice: Subject to any disclaimer, the term of this patent is extended or adjusted under 35 U.S.C. 154(b) by 513 days.

(21) Appl. No.: 18/033,705

(22) PCT Filed: Oct. 26, 2021

(86) PCT No.: PCT/IB2021/000736
§ 371 (c)(1),
(2) Date: Apr. 25, 2023

(87) PCT Pub. No.: WO2022/090797
PCT Pub. Date: May 5, 2022

(65) Prior Publication Data
US 2023/0397825 A1      Dec. 14, 2023

Related U.S. Application Data

(60) Provisional application No. 63/105,588, filed on Oct. 26, 2020.

(51) Int. Cl.
*A61B 5/0205*      (2006.01)
*A61B 5/00*      (2006.01)
*A61B 5/01*      (2006.01)
*A61B 5/021*      (2006.01)
*A61B 5/024*      (2006.01)

(52) U.S. Cl.
CPC ............ *A61B 5/02055* (2013.01); *A61B 5/01* (2013.01); *A61B 5/021* (2013.01); *A61B 5/024* (2013.01); *A61B 5/7267* (2013.01); *A61B 5/7282* (2013.01); *A61B 2560/0223* (2013.01); *A61B 2562/0271* (2013.01); *A61B 2562/029* (2013.01)

(58) Field of Classification Search
CPC ..... A61B 5/02055; A61B 5/021; A61B 5/024; A61B 5/01; A61B 5/7267; A61B 5/7282; A61B 2560/0223; A61B 2562/0271; A61B 2562/029
See application file for complete search history.

(56) References Cited

U.S. PATENT DOCUMENTS 6,221,025 B1      4/2001   Skoletsky
6,454,707 B1*    9/2002   Casscells, III ......... A61B 5/412
                                                                    600/300

(Continued)

OTHER PUBLICATIONS

International Search Report and Written Opinion issued in International Application No. PCT/IB2021/000736, date of mailing: Feb. 9, 2022, 18 pages.

*Primary Examiner* — Amanda L Steinberg
(74) *Attorney, Agent, or Firm* — Brown Rudnick LLP; Adam M. Schoen

(57) ABSTRACT

This disclosure provides methods and devices for evaluating a patient's heath by assessing the patient's thermoregulatory response to heat. For example, methods include applying heat to patient skin and measuring rate of temperature change. If the rate of temperature change exceeds a predetermined threshold, the patient can be identified as suffering from acute heart failure.

11 Claims, 2 Drawing Sheets

(56)  References Cited

U.S. PATENT DOCUMENTS

| | | | |
|---|---|---|---|
| 2003/0092975 A1* | 5/2003 | Casscells, III | A61B 5/412 |
| | | | 600/300 |
| 2003/0219719 A1* | 11/2003 | Bowman | A61B 5/413 |
| | | | 703/11 |
| 2008/0027330 A1* | 1/2008 | Naghavi | A61B 5/7275 |
| | | | 600/481 |
| 2008/0167572 A1* | 7/2008 | Stivoric | G01K 1/024 |
| | | | 374/E1.004 |
| 2008/0255471 A1* | 10/2008 | Naghavi | A61B 5/01 |
| | | | 600/549 |
| 2012/0123232 A1 | 5/2012 | Najarian et al. | |
| 2016/0166157 A1 | 6/2016 | Naghavi et al. | |
| 2018/0014734 A1* | 1/2018 | Rogers | A61B 5/0205 |
| 2019/0150761 A1 | 5/2019 | Sandgaard | |
| 2020/0050248 A1* | 2/2020 | Smith | G05B 15/02 |
| 2021/0378527 A1 | 12/2021 | Strasser et al. | |

* cited by examiner

METHOD AND APPARATUS FOR EARLY DETECTION OF WORSENING HEART FAILURE

CROSS-REFERENCE TO RELATED APPLICATIONS

This application is a national stage entry of PCT Application No. PCT/IB2021/000736, with an international filing date of Oct. 26, 2021, which claims priority to, and the benefit of, U.S. Provisional Application No. 63/105,588, filed Oct. 26, 2020, the content of which is incorporated by reference herein in its entirety.

TECHNICAL FIELD

This disclosure relates to methods and devices for detecting worsening heart failure.

BACKGROUND

Heart failure is a common condition in the United States. Over five million Americans have heart failure, with over 800,000 new cases diagnosed annually. This chronic condition is marked by episodes of acute decompensation, often referred to as worsening heart failure. Unfortunately, patient outcomes remain poor with a 5-year survival rate of approximately 50%. Early detection of worsening heart failure is crucial for improving prognosis of decompensated heart failure patients, as early detection can enable medical treatment to stop further decompensation and acute heart failure.

Existing approaches for early detection of worsening heart failure include monitoring water accumulation inside the lungs or monitoring blood pressure changes by implanting pressure sensors inside the patient's body. Unfortunately, neither approach is ideal. Monitoring accumulation of water inside the lungs only detects heart failure at later stages when water has already filled the lungs and decompensation is likely inevitable. Whereas, implanted sensors are invasive and carry many health risks, including the risk of a deadly infection.

SUMMARY

The invention recognizes that heart failure patients exhibit an impaired thermoregulatory ability. In response to heat stress, the impaired thermoregulatory ability results in a more rapid increase in body temperature as compared with a healthy patient (i.e., a patient without heart failure). The invention takes advantage of this insight to provide methods and devices for early detection of heart failure. In particular, the invention provides methods and devices that involve applying thermal energy to a patient's body and evaluating the patient's thermoregulatory response, which preferably involves measuring a rate of temperature change of the body, for example, measuring a rate of temperature change of the skin before sweating is initiated. The rate of temperature change is compared to a reference (e.g., a rate of temperature change from of a healthy patient or the rate of change from the same person when his heart failure is stable) to determine whether the patient may be suffering from heart failure. Because methods and devices of the invention can identify a patient as suffering from heart failure early, methods and devices of the invention allow for early clinical interventions that prevent further heart decompensation and provide life-saving therapies.

It is an insight of the invention that a patient suffering from heart failure (e.g., acute heart failure) exhibits elevated skin temperatures at a faster rate than in a patient that is not suffering from heart failure. Accordingly, a heart failure patient exposed to high ambient air environment (e.g., temperature over 35 degrees Celsius and more so at temperatures over 38 degrees C.) will experience a faster rate of skin temperature elevation than a patient not suffering from heart failure at the first few minutes (up to 30 minutes) before the onset of sweating and its evaporation. Because of this insight, the invention can provide non-invasive, diagnostic devices and methods thereof to measure and compare changes in skin temperature so as to allow for early detection of heart failure, which allows patients to receive or modify treatment regimens and/or avoid harmful stress.

In one aspect, the invention provides a method for assessing a subject's health status. Preferably, this includes identifying whether the subject has acute heart failure (i.e., worsening heart failure). Although, other types of health assessments are considered within the scope of the invention. The method involves applying heat to a portion of a subject's body and measuring a rate of temperate change of the body. Preferably, the portion of the body that is assessed includes skin, such as, skin from a subject's arm, leg, or abdomen. The method further includes comparing the rate of temperature change to a reference value and, based upon the comparison, assessing health status of the subject.

For example, in preferred embodiments, assessing whether the subject is suffering from acute heart failure involves measuring a rate of temperature change of the subject's body (e.g., skin) and when the rate of temperature change exceeds a reference value, the subject is identified as having acute heart failure. Preferably, the reference value is a rate of temperature change that was taken when the subject was in good health, i.e., not suffering from acute heart failure. Alternatively, the reference value may be a rate of change in temperature of a population of persons that do not have heart failure.

The step of applying heat may be performed with a covering that is placed around a portion of the subject's body. The covering can be, for example, a cuff that is dimensioned to fit around a subject's arm, leg, finger, or torso. Alternatively, the covering may be a device that, for example, resembles a heart rate monitor and is sized to fit around/onto a subject's finger. Advantageously, the area to be covered may be as small as 5 square centimeters. As such, in some embodiments, the covering may be a small patch that is applied to the subject and held in place by, for example, an adhesive.

Methods of the invention may use devices such as a covering (e.g., a cuff) with a heater that is operable to heat an interior of the covering.

The heater can generate the heat from conduction, convection or radiation sources for example:

Ultraviolet light, thermal conductive material, water perfused cuff, warm air blowing on the skin, infrared heat source Ideally, the interior of the covering may be heated to a temperature that is between 35 degrees Celsius and 45 degrees Celsius. The application of heat to the subject's body (e.g., skin) is preferably performed for approximately 15 minutes or until sweating is detected with the change in the absolute humidity sensing.

In the first few minutes, typically the first 2-3 minutes, the skin temperature will be elevated to approximately 33 degrees Celsius so as to provide calibrated baseline for all measurements. Following this initial calibration test the fast-thermal challenge will be performed and the skin will be exposed to higher temperatures of between about 38-45 degrees Celsius.

In some instances, the covering may further include a skin temperature sensor that measures online skin temperatures at least once every minute. There can also be more sensors. One or more additional sensors. The one or more additional sensors may serve to sense one or more additional aspects of the subject's health. For example, the one or more additional sensors may be suitable for measuring at least one of heart rate or blood pressure.

In preferred embodiments, the step of applying heat to the subject's body (e.g., skin) and the step of measuring the rate of temperature change are performed at least partially coincident with each other. That is, in preferred embodiments, an elevation of temperature change of the skin is measured simultaneously with the application of heat. Alternatively, heat may be applied, and following the application of heat, the rate of temperature change of the skin can be measured. The application of heat and measuring of temperature change can be made to the same area of the body. For example, on the same arm, leg, finger, or area of torso. Or, the application of heat and measurements of skin temperature elevation can be made at different areas of the body.

In preferred embodiments, the step of comparing a rate of temperature change to the reference value is performed with a computer program. The computer program may include a machine learning algorithm. The machine learning algorithm may be trained to determine a health status based at least in part on a comparison between the subject's rate of temperature change and a reference value. The reference value may be a calculation that is made by the machine learning algorithm based on the algorithm's training. Accordingly, in some instances, the method further comprises the step of providing training data to the machine learning algorithm, wherein the training data includes a plurality of rates of temperature changes with known patient health statuses.

Methods of the disclosure may be performed multiple times on the subject. For example, the method may be performed on at least two different days. On a first day, the subject may be in good health (i.e., not experiencing acute heart failure). The rate of temperature elevation made while the subject is in good health may serve as a baseline for assessing the subject when the subject experiences acute heart failure. Where the method is performed multiple days, is may be desirable that the method be performed under substantially the same environmental conditions on multiple days, the environmental conditions including room temperature, time of day hydration status. The method may further comprise reporting the health status to a physician. The method may further comprise inputting the results into a treatment system and enabling change of treatment parameters. For example, when worsening of heart failure is detected, change of temperature parameters may include more prolonged treatments at lower ambient temperatures.

In certain embodiments, methods of this disclosure may further include a calibration step to improve diagnostic accuracy. The calibration step may include raising the subject's skin temperature to approximately 33 degrees Celsius, which serves to calibrate baseline environmental conditions. Preferably, the subject will be asked to perform the test under the same environmental conditions each time the method is performed, for example, under the using the room temperature, same time of day and same hydration status (drinking a glass of water).

In another aspect, the disclosure provides a medical device for assessing a subject's health. The medical device includes a covering dimensioned for a portion of a subject's body, such as, an arm, leg, abdomen, or finger. The medical device may further include a heater that is operably connected to the covering and suitable for heating an interior surface of the covering and a sensor at least partially disposed within the interior of the covering. The sensor capable of measuring a temperature of the subject's body. In preferred embodiments, the device further includes a computer operably associated with said sensor, the computer designed to measure a rate of temperature change of the body and compare said rate of temperature change to a reference value.

The computer may be housed inside a control unit that is independent from the covering. The control unit may be connected to the covering by a wire. The computer may include a machine learning system, the machine learning system may be trained on training data including rates of temperature changes of patients with known patient outcomes. The covering may further include one or more additional sensors for measuring at least one of heart rate or blood pressure. The device may be designed to measure rates of temperature change, and, when the rate of temperature change is above the reference value, the computer is trained to identify the subject as having acute heart failure.

DETAILED DESCRIPTION

Figure 1:
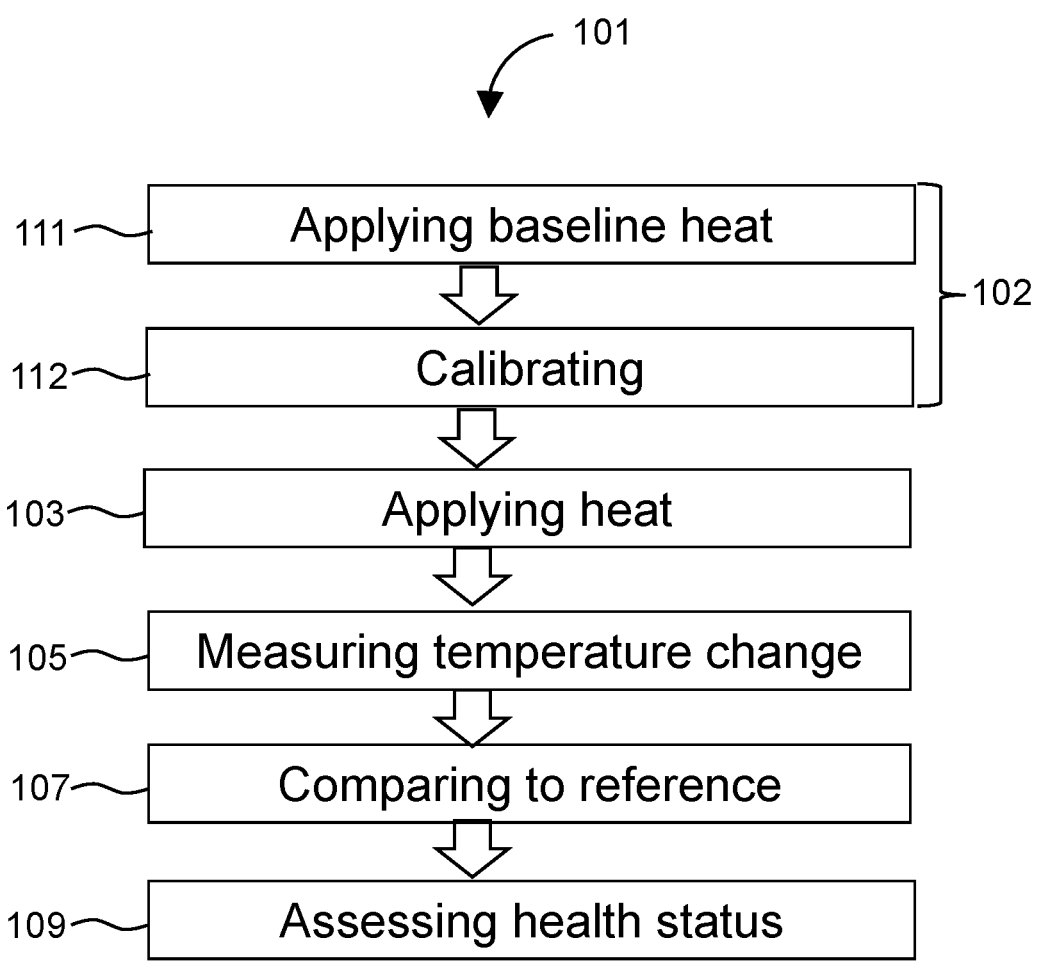
FIG. 1 diagrams a method for assessing health status.

There are at least two physical factors that enable the human body to regulate core and skin temperature: sweat evaporation, which locally cools down the area that has evaporated; and skin blood flow rate, which is regulated by the Cutaneous Vascular Conductance (CVC) and cools blood as it passes from the skin and to the core vasculature, cooling the core vasculature too. Typically, it takes approximately 15 minutes for a person to start sweating upon exposure to high ambient temperatures (e.g., temperatures greater than 38 degrees Celsius). During these 15 minutes, if a person is exposed to high ambient temperatures, that are higher than the core temperature (37 degrees Celsius) the skin blood flow is the primary method by which the body can cool down the skin. Following these 15 minutes sweating is initiated and evaporation sweat may cool the skin.

Once a person is placed in an ambient air temperature of, for example, 45 degrees Celsius, skin temperature starts to elevate quickly and at a rate that is dependent on skin blood flow volume. After about 15 minutes, sweating begins, and a second cooling mechanism protects the skin from overheating. The rate at which the skin temperature is elevated is well correlated to heart and fluid overload condition as vasodilatation, which enables the increased skin blood flow and its cooling, needs to occur. In normal subjects, vasodilatation occurs and enables skin blood flow that can be much higher than before the heat exposure. However, in heart failure patients this ability to vasodilate and increase the skin blood flow is attenuated. The reason attenuation in heart failure patients is that the body tries to maintain core vasculature blood flow and avoid hypotension in these already depressed cardiac function patients.

The ability to increase the skin blood flow and as a result to cool it down, in heart failure patients, is greatly attenuated. This is because the body tries to maintain core vasculature blood flow to vital organs thus preventing reduction of blood pressure. It does so at the expense of increasing the CVC and in turn cooling of the skin. As a result of the attenuated CVC and skin blood flow, upon exposure to elevated ambient temperature to levels above 38 degrees Celsius, the skin temperature of a heart failure patient will elevate at a much faster rate than in a healthy individual (i.e., a patient without heart failure).

For a given heart failure patient with a baseline correlation between his skin temperature elevation and ambient air temperature, changes in his heart function condition or his fluid overload status will in turn change this correlation. If a heart failure patient becomes decompensated, the elevation in his skin temperature, upon exposure to high ambient temperature, will be much faster than when the heart is compensated. This insight is realized by the invention to provide methods and devices for assessing a health status by measuring rate of temperature change of a patient's body upon application of heat and comparing the measured rate of temperature change to one or more references associated with a known health status.

FIG. 1 diagrams a method 101 for assessing health status. The method involves applying 103 heat to a portion of a subject's body (e.g., skin) and measuring 105 a rate of temperate change of the body. The steps of applying 103 heat and measuring 105 rate of temperature change are preferably performed coincident with one another. The method further includes comparing 107 the rate of temperature change to a reference value and then assessing 109 a health status of the subject.

In preferred embodiments, the method 101 further includes a calibrating 102 step, which serves to improve accuracy of the method as a diagnostic tool. The calibrating 102 may include applying a baseline heat 111 (e.g., applying heat at a temperature of approximately 33 degrees Celsius). The method may further include the step of calibrating 112 at the baseline skin temperature (lower than the threshold of sweating and typically 33 degrees C.).

After calibrating, methods of the invention involve applying a thermal challenge. The thermal challenge may involve applying 103 heat to a portion of the subject's body, preferably the skin, may involve contacting a heater to the subject's skin, or holding the heater in the near vicinity the subject's skin for approximately 10-20 minutes, and preferably 15 minutes. This may be performed using an apparatus such as a covering, sleeve, chamber, cuff, etc., that is dimensioned for fitting around a portion of the subject's body, such as, an arm, leg, foot, finger, head, or torso. For example, the apparatus, e.g., cuff, may have a heater operably associated with an interior surface of the cuff. When the heater is on, the heater may supply heat to an interior region of the cuff. In other embodiments, the apparatus may comprise a patch with, for example, an adhesive that allows the covering to attach and remain in place on the subject's body. The patch may cover an area that is as small as 5 square centimeters. The patch may include a thermo-conductive material connected with a heater to heat a surface of the patch where the patch is applied to the subject's body.

Application 103 of heat can be performed using a heater. Such as an electrical heater or any other type of heater (infrared, water perfused, ultraviolet source, air blower). An electric heater is an electrical device that converts an electric current into heat. The heating element inside the electric heater may be an electrical resistor and may work on the principle of Joule heating: an electric current passing through a resistor that will convert the electrical energy into heat energy. The electrical heater may be powered by a battery. The heater is preferably suitable to apply a temperature of about 35 degrees Celsius to and 45 degrees to the subject via the apparatus (e.g., cuff).

Measuring 105 temperature change may be performed using a temperature sensor. A temperature sensor is an electronic device that measures the temperature of its environment and converts the input data into electronic data to record, monitor, or signal temperature changes. There are many different types of temperature sensors. Some temperature sensors require direct contact with the physical object (e.g., skin) that is being monitored (contact temperature sensors), while others indirectly measure the temperature of an object (non-contact temperature sensors, e.g., infrared sensors). Any type of temperature sensor may be suitable for use with the device. The temperature sensor is preferably connected to a computer comprising an algorithm that measures, records, and stores changes in temperature over time.

There can also be a relative and absolute humidity sensor inside the cuff that senses when sweating has been initiated. The relative humidity sensor (or the absolute humidity sensor) can detect baseline low absolute humidity, at the onset of the thermal challenge (e.g., method 101). Once the humidity has elevated it can be observed that sweating has started and the specific challenge will be analyzed until that point of sweating initiation. The method may involve measuring, with one or more humidity sensors, a time to onset of sweating.

After measuring 105 temperature change, the measured temperature change is compared to a reference value to assess 109 health status. In preferred embodiments, the reference value is a baseline measurement of a rate of temperature change taken from the subject when the subject was in good health, e.g., when the subject was not suffering from acute heart failure or relative to his last measurements. To determine whether the subject is in good health (not suffering from acute heart failure) and thus, acquire the baseline measurement, the physician may assess the health of the subject heart using one or more tests, such as an electrocardiogram or chest X-ray. The physician may also listen to the subject's heart using a stethoscope. Or require that the subject perform a number of exercise tests. If the tests show that the subject is in good health (i.e., not suffering from heart failure) the rate of temperature change of the subjects skin may server as a baseline measurement for future analyses to detect when the patient is suffering from acute heart failure.

Alternatively, the reference value may be a value taken from a population of people known not to have heart failure. The population may comprise a population of people with similar health features to the subject. Such as, same gender, body-weight-index score, height, age, etc.

Comparing 107 involves determining a similarity or dissimilarity between the change in body temperature of the subject and the reference value. This may be performed using a computer. The computer may host a machine learning algorithm, as discussed below. When the rate of temperature change exceeds the reference value, the subject may assessed 109 as having acute heart failure.

In embodiments in which a machine learning system is employed to assess the subject's health status, methods of the invention may further include the step of providing training data to the machine learning algorithm, wherein the training data comprising a plurality of rates of temperature changes with known patient health statuses.

Accordingly, certain aspects of the invention may rely on a computer system. The system may include a processor coupled to a memory subsystem including instructions executable by the processor to cause the system to measure temperature change from signals received by one or more sensors and to determine a correlation between the measured temperature changes and one or more reference values (e.g., temperature changes associated with a healthy heart) to provide a predictive output.

The system may include at least one computer. The computer may include a processor coupled to a tangible, non-transitory memory device and at least one input/output device. Thus the system may include at least one processor coupled to a memory subsystem. Processor refers to any device or system of devices that performs processing operations. A processor will generally include a chip, such as a single core or multi-core chip (e.g., 12 cores), to provide a central processing unit (CPU). A processor may be any suitable processor such as the microprocessor sold under the trademark XEON E5-2620 v3 by Intel (Santa Clara, CA).

The memory subsystem may contain one or any combination of memory devices. A memory device is a mechanical device that stores data or instructions in a machine-readable format.

Figure 2:
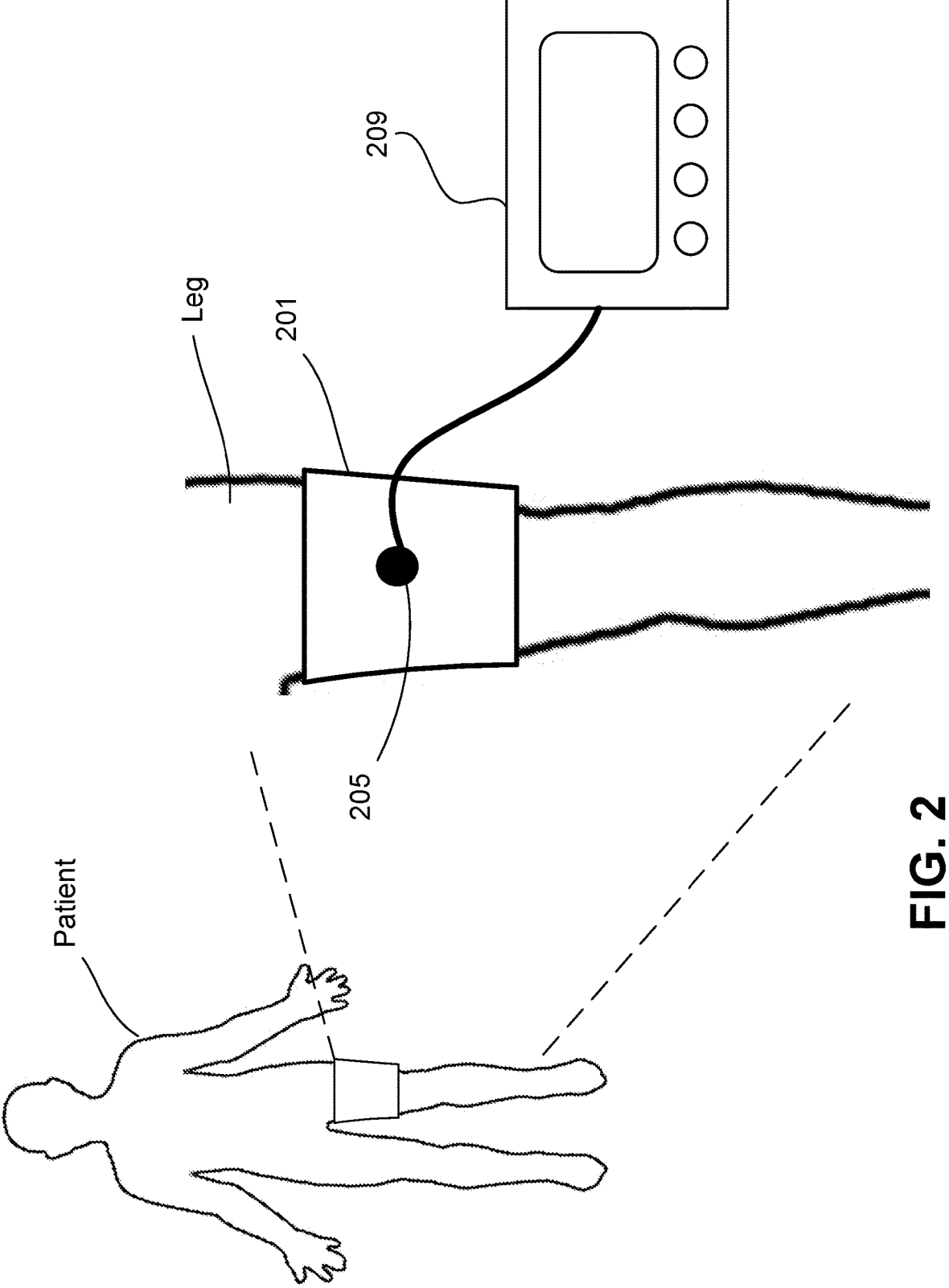
FIG. 2 shows a device according to aspects of the invention.

FIG. 2 shows a device according to aspects of the invention. The device comprises a covering 201, i.e., a cuff, dimensioned for receiving a portion of a subject's body, such as, an arm, finger, foot, leg, head, chest or torso. The covering may be a thermal cuff designed to generate heat. The thermal cuff may, for example, generate heat within an interior of the cuff to a temperature between 35 degrees Celsius and 50 degrees Celsius. The device can further include a sensor 205 that is at least partially disposed within an interior of the covering 201 and capable of measuring a temperature of the subject's body. The device may further include a computer (not shown) operably associated with said sensor 205, the computer designed to measure a rate of temperature change of the body and compare said rate of temperature change to a reference value. The computer can be housed in a control unit 209 that is independent from the cuff.

The computer may include a machine learning system, the machine learning system may be trained on training data comprising rates of temperature changes of patients with known patient outcomes. Any of several suitable types of machine learning systems may be used. Suitable machine learning types may include neural networks, decision tree learning such as random forests, support vector machines (SVMs), association rule learning, inductive logic programming, regression analysis, clustering, Bayesian networks, reinforcement learning, metric learning, and genetic algorithms. Moreover, the device may include one or more additional sensors for measuring at least one of heart rate or blood pressure.

In certain aspects, the invention provides methods and devices to detect changes in heart failure status and alert the patient and his physician to seek medical treatment. A local thermal challenge/test can be applied to a patient's skin area. The thermal test can be performed in various ways and on different locations on the body. The apparatus can be a cuff that is placed around an area of the body, e.g., an arm, or leg, finger, or abdomen.

The cuff can generate heat from a battery powered heat source, or it can generate heat by blowing through a thermal resistor and creating warm air that is directed to the skin surface under the cuff or directly without a cuff.

The temperature that is generated inside the cuff or directly on the skin can be between 35 degrees Celsius and 45 degrees Celsius, and it can be applied to any area in any place on the body. The skin temperature may be monitored as it elevates using a local online skin temperature sensor. The area exposed to heat may be as small as 5 square centimeters to as large as a covering that covers the lower part of the body.

In some embodiments, each patient will have a baseline measurement taken when the patient is diagnosed to be compensated and feeling good in good health. Once every few days the patient may perform the same thermal challenge at approximately the same location and under the same thermal parameters. If the skin temperature elevation is faster than the baseline it may indicate deterioration of the patient's fluid overload status or heart function.

In some embodiments, monitoring may be performed as the initial step of device treatment and the results of the monitoring can be inputted into the algorithm of the device thus changing the therapeutic parameters for the specific treatment.

In case there is a deterioration of the heart function (faster elevation of the skin temperature) the treatment will be performed at lower ambient temperatures to avoid heat stress and for longer durations to ensure sufficient fluid removal.

The monitoring results may be sent to the treating physician and there will be cutoff values that will alarm and send this alarm to the treating physician.

In certain embodiments, monitoring may be continued once the patient is in the treatment episode and has started to sweat. Heart rate and blood pressure may be monitored during the treatment to confirm or support heart status. If heart rate is elevated above a baseline it may indicate deterioration. If during the treatment the core temperature elevates to a higher value and at, for example, a faster elevation rate it may also be an indication that the heart function status has deteriorated.

In some embodiments, the apparatus can be a local heater that generates air through a flexible pipe that, for example, blows air to the skin and is attached to the body and ensures a specific distance and a specific angle to the surface of the skin. At a middle of the area that is being heated there may be an online skin temperature sensor that is connected to a small and mobile controller with stored historical values of the skin temperature and results of past thermal challenges.

Initially the baseline skin temperature may be measured and if the baseline is different than in past measurements the heater may either cool or heat the skin to a same baseline value. From this specific baseline value, we may initiate the thermal challenge. The graph of the skin temperature values over time may be displayed as a values baseline graph in the control panel. The control panel may be battery operated and may send information and parameters of the heat test online to a treating physician.

Instances where the skin temperature elevates at a faster rate than a baseline elevation gradient may indicate that skin blood flow is attenuated, thereby indicating reduced heart function may be sending signals to maintain core blood flow by constricting blood vessels or disabling vasodilatation. Once the system detects that this elevation is higher than the baseline measured elevation (e.g., taken for each patient at a compensated state) the system can alert and send the data to the treating physician.

Furthermore, during treatment with a treatment device that covers larger body surface area, for example, as described in co-owned, Patent Application No. PCT/IB2020/000594, filed Jul. 17, 2020, which is incorporated by reference herein, the core body temperature may be elevated faster than baseline measurements and may indicate reduction in heart function. If heart rate is increased under the same thermal challenge conditions, it may also indicate reduction in heart function and decompensation and an alert will be shown and sent.

The patient may need to be hydrated prior to the thermal challenge and it may be recommended to perform the challenge at the same time in the day and approximately 15 minutes after drinking a glass of water.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A non-invasive method for providing detection of heart failure of a subject, the method comprising:

applying, via a mobile and wearable device, thermal energy to a portion of a subject's skin, the device being placed entirely around a portion of at least one of a torso, arm, and leg of the subject;

evaluating the subject's thermoregulatory response to the application of thermal energy, wherein said evaluating comprises:

performing, for about 2 to 3 minutes, an initial calibration step comprising raising the subject's skin temperature to approximately 33 degrees Celsius to calibrate baseline environmental conditions;

exposing the subject's skin to higher temperatures, via application of the thermal energy, of between about 38 degrees Celsius and 45 degrees Celsius;

measuring a rate of temperature change of the skin before the onset of sweating; and comparing said rate of temperature change to a reference value to thereby assess a health status of the subject, wherein the reference value comprises a rate of change in temperature that was measured when the subject was in good health and not suffering from or experiencing heart failure.

2. The method of claim 1, wherein providing detection of heart failure of a subject comprises identifying that the subject has acute or worsening of a heart failure condition.

3. The method of claim 1, wherein, when the rate of temperature change exceeds the reference value, the subject is identified as having acute heart failure.

4. The method of claim 1, wherein the device further comprises one or more additional sensors for measuring at least one of heart rate or blood pressure.

5. The method of claim 1, wherein the device comprises a heater, the heater operable to heat an interior of the device to a temperature that is between 35 degrees Celsius and 45 degrees Celsius.

6. The method of claim 1, wherein the step of exposing the subject's skin to higher temperatures is performed for approximately 15 minutes or until sweating is detected with change in absolute humidity sensing.

7. The method of claim 6, wherein the step of exposing the subject's skin to higher temperatures and the step of measuring the rate of temperature change are performed at least partially coincident with each other.

8. The method of claim 1, wherein the step of comparing the rate of temperature change to the reference value is performed with a computer program.

9. The method of claim 8, wherein the computer program comprises a machine learning algorithm.

10. The method of claim 9, further comprising the step of providing training data to the machine learning algorithm, the training data comprising a plurality of rates of temperature changes with known patient health statuses.

11. The method of claim 1, further comprising reporting the health status to a physician or inputting the results into a treatment system and enabling change of treatment parameters.

* * * * *